United States Patent [19]

Petrocine

[11] Patent Number: 4,562,257

[45] Date of Patent: Dec. 31, 1985

[54] PREPARATION OF SUBSTITUTED AND UNSUBSTITUTED 2-CARBAMOYL NICOTINIC AND 3-QUINOLINECARBOXYLIC ACIDS

[75] Inventor: David V. Petrocine, Saddle River, N.J.

[73] Assignee: American Cyanamid Company, Stamford, Conn.

[21] Appl. No.: 549,045

[22] Filed: Nov. 7, 1983

[51] Int. Cl.[4] .............. C07D 213/803; C07D 215/54; C07D 401/04

[52] U.S. Cl. .................................. 546/169; 546/275; 546/321; 546/167; 546/336

[58] Field of Search .................... 546/169, 318, 116

[56] References Cited

U.S. PATENT DOCUMENTS 4,337,340  6/1982  Schmidt et al. .................. 546/11 X

*Primary Examiner*—Glennon H. Hollrah
*Assistant Examiner*—D. B. Springer
*Attorney, Agent, or Firm*—H. G. Jackson

[57] ABSTRACT

The invention provides a process for the preparation of substituted and unsubstituted 2-carbamoyl nicotinic and 3-quinolinecarboxylic acids.

9 Claims, No Drawings

PREPARATION OF SUBSTITUTED AND UNSUBSTITUTED 2-CARBAMOYL NICOTINIC AND 3-QUINOLINECARBOXYLIC ACIDS

The present invention is a novel method for the preparation of substituted and unsubstituted 2-carbamoyl nicotinic and 3-quinolinecarboxylic acids of formula (I):

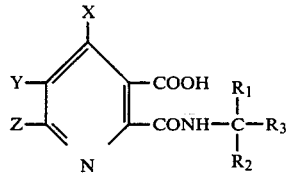

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together, along with the carbon to which they are attached, they may represent $C_3$–$C_6$ cycloalkyl optionally substituted with methyl, and when $R_1$ and $R_2$ are not the same, the optical isomers thereof; $R_3$ is CN or

W is O or S; X is hydrogen, or $C_1$–$C_4$ alkyl, Y is hydrogen, halogen, $C_1$–$C_4$ alkyl, $C_1$–$C_4$ alkoxy, trifluoromethyl, trichloromethyl, difluoromethoxy, diloweralkylamino, $C_1$–$C_4$ alkylthio, phenyl, phenoxy, or phenyl or phenoxy substituted with one $C_1$–$C_4$ alkyl, $C_1$–$C_4$ alkoxy or halogen; Z represents hydrogen, $C_1$–$C_4$ alkyl, trifluoromethyl, trichloromethyl, phenyl or phenyl substituted with one $C_1$–$C_4$ alkyl, $C_1$–$C_4$ alkoxy or halogen; and, when taken together, Y and Z may form a ring in which YZ are represented by the structure: —($CH_2$)$_n$—, where n is an integer of 3 to 5, provided that X is hydrogen; or YZ is

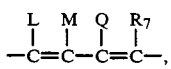

where L, M, Q and $R_7$ each represent hydrogen, halogen, $C_1$–$C_4$ alkyl, $C_1$–$C_4$ alkoxy, $C_1$–$C_4$ haloalkyl, difluoromethoxy, diloweralkylamino, $C_1$–$C_4$ alkylthio, nitro, phenyl, phenoxy, or monosubstituted phenyl or phenoxy where the substituent is one $C_1$–$C_4$ alkyl, $C_1$–$C_4$ alkoxy or halogen; with the proviso that only one of L, M, Q or $R_7$, may represent a substituent other than hydrogen, halogen, $C_1$–$C_4$ alkyl or $C_1$–$C_4$ alkoxy, comprising, reacting an anhydride of formula (II)

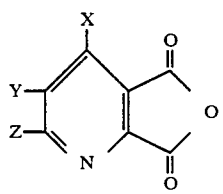

wherein X, Y and Z are as described for formula (I) above, with from 1 to 1.5 molar equivalents of an aminonitrile, aminocarboxamide or aminothiocarboxamide of formula (III)

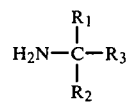

wherein $R_1$, $R_2$ and $R_3$ are as described for formula (I) above at from 5° to 45° C. and preferably 5° to 30° C., in a solvent system containing a minimum of 4 molar equivalents of pyridine, 4-picoline, 2-picoline, mixed picolines or quinoline, used either as the reaction solvent or as a co-solvent, with other organic solvents, for several hours.

The above reaction may be graphically illustrated as indicated in Flow Diagram (I) below.

FLOW DIAGRAM (I)

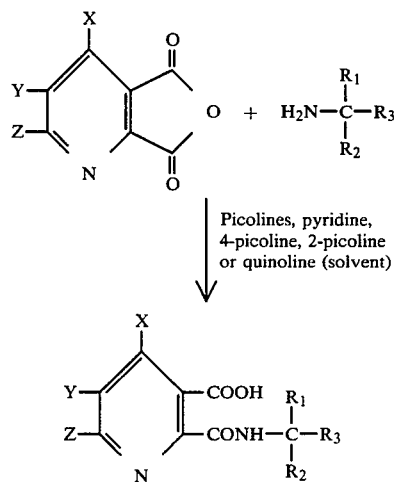

wherein X, Y Z, $R_1$, $R_2$ and $R_3$ are as described above.

The discovery that the addition of pyridine, 4-picoline, 2-picoline, mixed picolines and quinoline improves the selectivity of the reaction between formula (II) anhydrides and formula (III) amines to give predominantly 2-carbamoyl nicotinic and 3-quinolinecarboxylic acids is unique, as previous reactions in the absence of these compounds yielded substantial amounts of the undesired 3-carbamoyl picolinic or quinaldic acids (25 to 35%), as would normally be expected in the reaction of an unsymmetrical anhydride with an amine as indicated in Flow Diagram (II) below.

FLOW DIAGRAM (II)

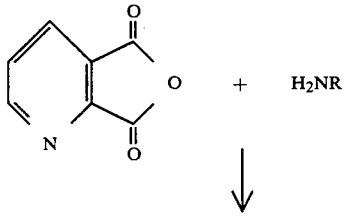

-continued
FLOW DIAGRAM (II)

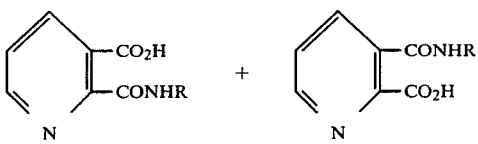

The process of the invention is of particular importance for the preparation of the herbicidally effective formula (IV) 2-(4,4-disubstituted-5-oxo(or thiono)-2-imidazolin-2-yl)nicotinic acids and 3-quinolinecarboxylic acids, described in the copending application for U.S. Patent of Marinus Los, Ser. No. 382,041 filed May 25, 1982, by reaction of an appropriately substituted formula (II) anhydride with an aminocarboxamide, aminothiocarboxamide or aminonitrile depicted by formula (III) to yield formula (I) carbamoyl nicotinic, quinolinecarboxylic acids selectively over the carbamoyl picolinic or quinaldic acid. The method of the present invention improves the isomer ratio of the desired nicotinic- and 3-quinolinecarboxylic acid isomers significantly, affording the desired isomers in 80 to 90% yields. The resulting formula (I) substituted 2-carbamoyl nicotinic- and 3-quinolinecarboxylic acids are readily converted to herbicidally effective formula (IV) 2-(4,4-disubstituted-5-oxo(or thiono)nicotinic and 3-quinolinecarboxylic acids by reaction with from 2 to 20 equivalents of an aqueous or aqueous alcoholic sodium or potassium hydroxide and from 0 to 10 molar equivalents of 30 to 90% aqueous hydrogen peroxide at a temperature of from 20° to 100° C. and thereafter acidifying the thus formed reaction mixture to a pH between 2 and 4 with a mineral acid as shown in illustration III below. The process of this invention is described in the copending application for U.S. Patent of Don W. Long, Kenneth D. Lotts and Jerry M. Barton, Ser. No. 381,818, filed May 25, 1982 and incorporated herein by reference thereto.

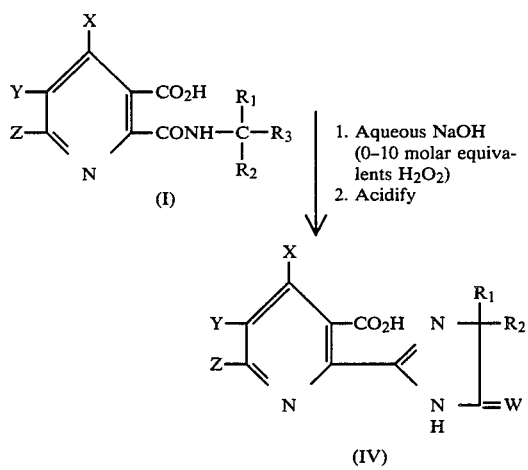

wherein X, Y, Z, $R_1$ and $R_2$ are as described for formula (I).

The present invention is further illustrated by the following non-limiting examples.

EXAMPLE 1

Comparison of effect of pyridine, 4-picoline, mixed picolines and quinoline on the formation of substituted 2-carbamoyl-3-quinolinecarboxylic acid

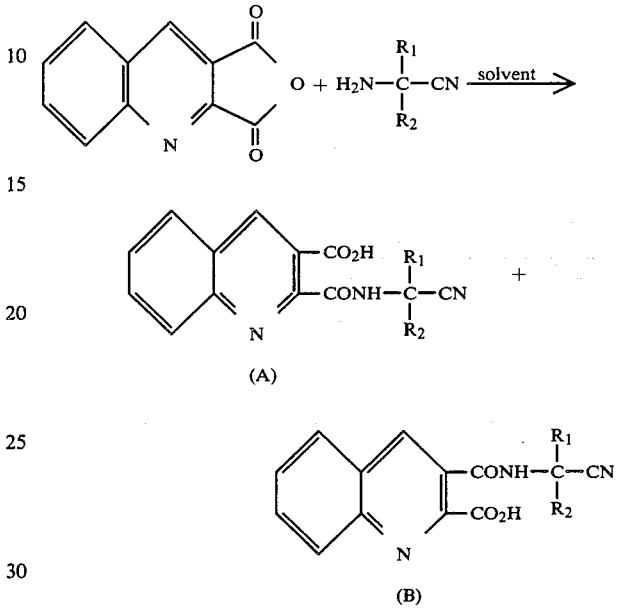

The aminonitrile (24.2 mmol) in 5 mL of the solvent used for the reaction is added dropwise over a ten minute period to a stirred solution of 2,3-quinolinedicarboxylic anhydride (20.06 mmol) in 100 mL of solvent. The resulting mixture is stirred until reaction is complete (usually one-half to three hrs) at room temperature and an aliquot of the mixture assayed by high performance liquid chromatography to determine the weight ratio of the desired 2-carbamoyl-3-quinolinecarboxylic acid (A) to the undesired 3-carbamoyl 2-quinolinecarboxylic acid (B).

The results of these experiments are reported in Table I below and demonstrate the effectiveness of the use of pyridine, 4-picoline, mixed picolines and quinoline for increasing the ratio of the desired isomer (A).

TABLE I

Effect of pyridine, mixed picolines, 4-picoline, and quinoline on the formation of 2-carbamoyl-3-quinolinecarboxylic acid

| Solvent | Isomer ratio A/B |
| --- | --- |
| Acetonitrile | 3.1/1 |
| Toluene | 3.3/1 |
| Dimethylformamide | 6.3/1 |
| Dimethoxyethane | 3.9/1 |
| Methylethylketone | 3.6/1 |
| Furan | 3.5/1 |
| 2,6-Lutidine | 5.7/1 |
| Pyridine | 19.2/1 |
| Mixed picolines | 10.3/1 |
| 4-Picoline | 19.0/1 |
| Quinoline | 15.7/1 |

EXAMPLE 2

Effect of solvent on the yield of
2-[(1-cyano-1,2-dimethylpropyl)-carbamoyl]nicotinic acid

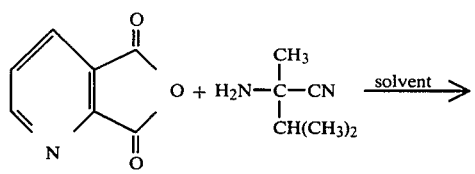

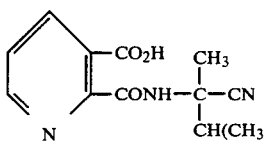

The aminonitrile (0.1375 mol) is added over a ten minute period to a stirred solution of 2,3-pyridinedicarboxylic anhydride (0.125 mol) in 65 ml of the desired solvent, while maintaining the temperature of the reaction mixture below 35° C. Upon completion of the aminonitrile addition the reaction mixture is stirred for one and one-half hrs and then weighed and analyzed by high performance liquid chromatography for the desired 2-carbamoyl nicotinic acid.

The results of these experiments are summarized in Table II below, which demonstrates an increase in yields of the desired 2-carbamoyl nicotinic acid when pyridine, mixed picolines, 4-picoline or 2-picoline are used as the reaction solvent.

TABLE II

Effect of solvent on the formation of 2-carbamoyl nicotinic acid

| Solvent | % Yield |
|---|---|
| Pyridine | 85.8 |
| 4-Picoline | 90.5 |
| Mixed picolines | 86.8 |
| 2-picoline | 81.9 |
| Thiophene | 65.2 |
| Acetonitrile | 65.5 |
| THF | 70.7 |
| Nitrobenzene | 59.6 |
| N,N—dimethylaniline | 66.7 |
| Dimethoxyethane | 66.4 |
| 1,2-Dichloroethane | 62.6 |
| DMSO | 74.3 |
| DMF | 78.6 |
| Quinoline | 72.6 |

EXAMPLE 3

Effect of stoichiometry of 4-picoline on the formation of 2-[(1-cyano-1,2-dimethylpropyl)-carbamoyl]nicotinic acid

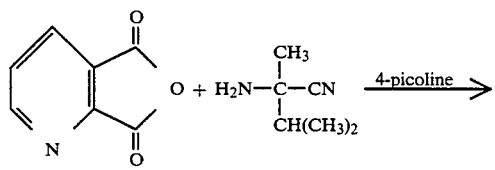

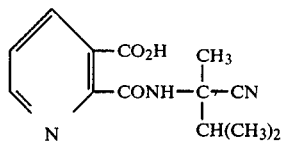

The aminonitrile (0.1375 mol) is added over a ten minute period to a stirred solution of 2,3-pyridinedicarboxylic anhydride (0.125 mol) in from 4 to 10 molar equivalents of 4-picoline while maintaining the temperature of the reaction mixture in a range between 10° to 25° C. Upon completion of the aminonitrile addition, the reaction mixture is stirred for one and one-half hrs and then weighed and analyzed by high performance liquid chromatography to determine the yield of the desired 2-carbamoyl nicotinic acid.

The results of these experiments are summarized in Table III below, which demonstrates increases in yields of the desired 2-carbamoyl nicotinic acid, utilizing from 4 to 10 equivalents of 4-picoline.

TABLE III

Effect of stoichiometry of 4-picoline on the formation of 2-carbamoyl nicotinic acid

| 4-Picoline molar equivalents | % Yield 2-carbamoyl nicotinic acid |
|---|---|
| 4.4 | 70.5 |
| 6.4 | 83.8 |
| 8.0 | 88.0 |
| 10.0 | 88.4 |

EXAMPLE 4

Preparation of 2-[(1-carbamoyl-1,2-dimethylpropyl)-carbamoyl]-3-quinolinecarboxylic acid

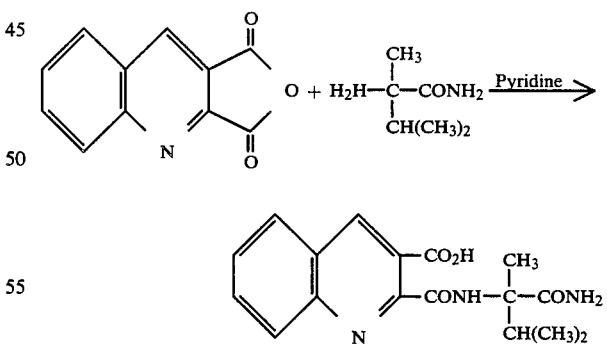

The aminoamide (24.25 mmol) is added over a two hour period to a solution of 2,3-quinolinedicarboxylic anhydride (20.06 mmol) in pyridine (100 mL) while maintaining the reaction mixture at room temperature. The mixture is allowed to stir at room temperature for one-half hour. Analysis of the isomer distribution of the reaction products by high performance liquid chromatography shows an 8.9/1 ratio of the desired 2-carbamoyl-3-quinolinecarboxylic acid.

EXAMPLE 5

Preparation of 2-(4-isopropyl-4-methyl-5-oxo-2-imidazolin-2-yl)-3-quinolinecarboxylic acid

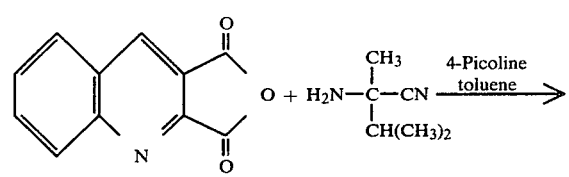

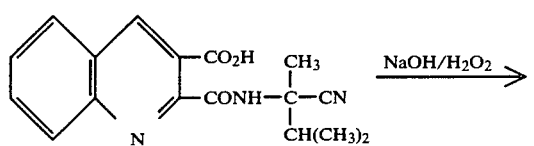

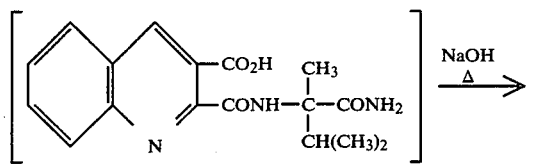

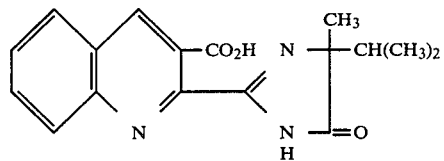

2-Amino-2,3-dimethylbutyronitrile (0.393 mol) is added over 40 minutes to a stirred solution of 2,3-quinolinedicarboxylic anhydride (0.376 mol) in 4-picoline (338 g, 3.63 mol) and toluene (52 g), while maintaining the temperature at 40° to 43° C. The reaction mixture is stirred at 40° to 43° C. for one hour. Aqueous sodium hydroxide (218 g, 25%, 1.36 mol) and then toluene 378 g) are added and the mixture stirred at 55° to 60° C. for approximately 15 minutes. The lower aqueous basic phase is separated off and the product extracted from organic phase with water. The aqueous phase is washed with toluene. A portion of the aqueous phase (25.8 g) is treated with 25% aqueous sodium hydroxide (10 g) and 3.7 equivalents of hydrogen peroxide at 65°–70° C. for one hour, then additional 50% aqueous sodium hydroxide (14.5 g) is added and the reaction mixture is allowed to stir for one hour at 65° to 70° C. The mixture is cooled to 25° to 30° C., and the pH of the mixture adjusted to 1.5 with concentrated sulfuric acid. The product 2-(4-isopropyl-4-methyl-5-oxo-2-imidazolin-2-yl)-3-quinolinecarboxylic acid (17.3 g) is isolated by filtration.

EXAMPLE 6

Preparation of 2-[1-carbamoyl-1,2-dimethylpropyl)carbamoyl]nicotinic acid

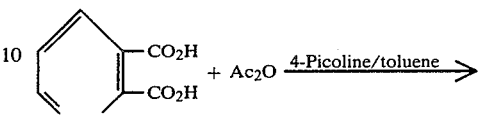

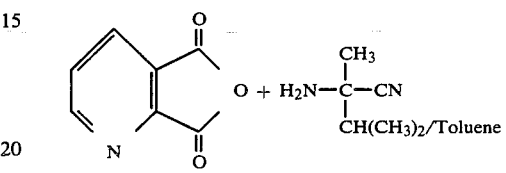

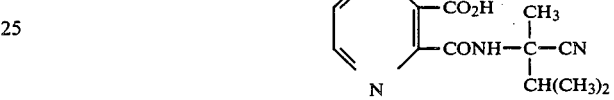

2,3-Pyridinedicarboxylic acid (16.7 g, 0.10 mol) is added all at once to a stirred solution of acetic anhydride (10.7 g, 0.105 mol) in 4-picoline (74.4 g, 0.8 mol) and toluene (4.52 mL) under a nitrogen atmosphere. After stirring for two and one-half hours at room temperature the resulting 2,3-pyridinecarboxylic anhydride solution is added to a stirred solution of 2-amino-2,3-dimethylbutyronitrile (0.11 mol) containing 50% on a weight basis of toluene, under a nitrogen atmosphere while maintaining the temperature of the reaction mixture at 10°–12° C. by controlling the addition rate of the anhydride solution. The resulting reaction mixture is stirred for one hour at 10°–12° C. and weighed. Analysis of the reaction mixture by high performance chromatography shows the formation of the desired 2-carbamoyl nicotinic acid in 88.9% yield.

EXAMPLE 7

Preparation of 2-(4-isopropyl-4-methyl-5-oxo-2-imidazolin-2-yl)nicotinic acid

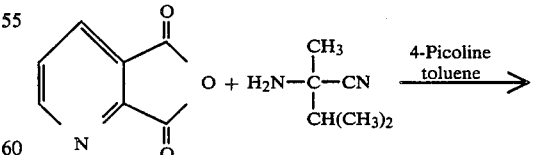

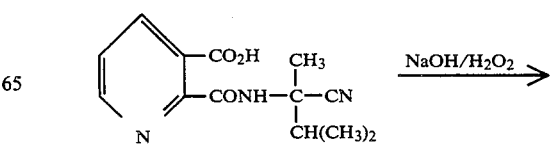

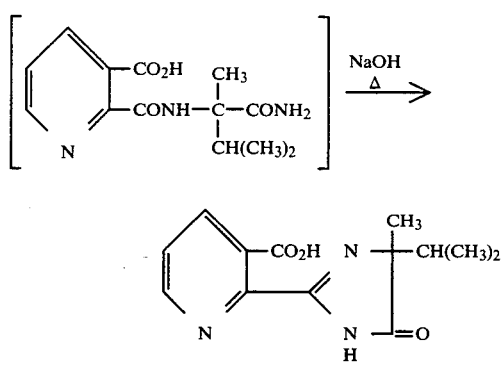

2-Amino-2,3-dimethylbutyronitrile (273.27 g, 94% purity, 2.287 mol) is added to a stirred solution of 2,3-pyridinedicarboxylic anhydride 333.3 g, 0.98 mol) in 4-picoline (1600 mL) under a nitrogen atmosphere while maintaining the temperature of the reaction mixture at 8° to 12° C. The resulting mixture is stirred for one and one-half hours at 8° to 12° C. Analysis of the reaction mixture by high performance liquid chromatography shows the formation of the desired 2-[(1-carbamoyl-1,2-dimethylpropyl)carbamoyl]nicotinic acid in 84.1% yield. The product is isolated by dilution of the reaction mixture with toluene (1600 mL), and extraction into aqueous sodium hydroxide (800 mL, 50% NaOH, in 532 mL water) at 35° to 40° C. The basic extract is washed with toluene (1600 mL) at 35° to 40° C., and the basic solution of the product (1778.0 g) is separated off. Additional aqueous sodium hydroxide (80 g, 50%) is added to one-half of the stirred basic extract and the solution heated to 40° C. Aqueous hydrogen peroxide (221 g, 50% 6.5 mol) is then added over one hour and 15 minutes at 40° to 45° C. and the reaction mixture is allowed to stir at 40°-45° C. for two hours. The reaction mixture is then heated to 70° C. and allowed to stir for two hours to complete the formation of the 2-(4-isopropyl-4-methyl-5-oxo-2-imidazolin-2-yl)nicotinic acid which is isolated by acidification, and filtration.

EXAMPLE 8

Postemergence herbicidal evaluation of test compounds

The postemergence herbicidal activity of the compounds prepared by the process of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ®20, a polyoxyethylene sorbitan monolaurate surfactant of Atlas Chemical Industries, in sufficient quantities to provide the equivalent of about 0.16 kg to 10 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table IV below.

| Rating System | % Difference in Growth from the Check* |
|---|---|
| 0 - No Effect | 0 |
| 1 - Possible effect | 1-10 |
| 2 - Slight effect | 11-25 |
| 3 - Moderate effect | 26-40 |
| 5 - Definite injury | 41-60 |
| 6 - Herbicidal effect | 61-75 |
| 7 - Good herbicidal effect | 76-90 |
| 8 - Approaching complete kill | 91-99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (Echinochloa crusgalli) |
| Green foxtail | (Setaria viridis) |
| Purple Nutsedge | (Cyperus rotundus L.) |
| Wild Oats | (Avena fatua) |
| Quackgrass | (Agropyron repens) |
| Field Bindweed | (Convolvulus arvensis L.) |
| Cocklebur | (Xanthium pensylvanicum) |
| Morningglory | (Ipomoea purpurea) |
| Ragweed | (Ambrosia artemisiifolia) |
| Velvetleaf | (Abutilon theophrasti) |
| Barley | (Hordeum vulgare) |
| Corn | (Zea mays) |
| Rice | (Oryza sativa) |
| Soybean | (Glycine max) |
| Sunflower | (Helianthus annus) |
| Wheat | (Triticum aestivum) |

TABLE IV

POST-EMERGENCE TESTS - RATES IN KG/HA

| Compound | RATE | BARNY ARDGR | GREEN FOX | P NUT SEDGE | WILD OATS | QUACK GRASS | FLD D IHOWO | MRNGL RY SP |
|---|---|---|---|---|---|---|---|---|
| 2-(4-Isopropyl-4- | 10.000 | 9.0 | 9.0 | 9.0 | 9.0 | | | 7.0 |
| methyl-5-oxo-2- | 2.000 | 9.0 | 9.0 | 9.0 | 9.0 | | | 0.0 |
| imidazolin-2-yl)- | 1.000 | 9.0 | 9.0 | 9.0 | 9.0 | 9.0 | 0.0 | 0.0 |
| nicotinic acid | .500 | 9.0 | 9.0 | 8.7 | 9.0 | 9.0 | 9.0 | 0.0 |
| | .250 | 8.9 | 9.0 | 8.8 | 9.0 | 9.0 | 9.0 | 0.9 |
| 2-(4-Isopropyl- | 0.000 | 9.0 | 9.0 | 9.0 | 9.0 | 9.0 | 9.0 | 9.0 |
| 4-methyl-5-oxo- | 4.000 | 9.0 | 9.0 | 9.0 | 9.0 | 9.0 | 9.0 | 0.5 |
| 2-imidazolin-2- | 2.000 | 9.0 | 9.0 | 0.5 | 9.0 | 9.0 | 9.0 | 0.3 |
| yl)-3-quinoline- | 1.000 | 9.0 | 9.0 | 0.3 | 9.0 | 8.9 | 8.7 | 0.3 |
| carboxylic acid | .800 | 9.0 | 8.8 | 6.8 | | 8.8 | 8.8 | 6.8 |
| | .500 | 8.9 | 8.9 | 7.6 | 9.0 | 8.6 | 8.3 | 7.7 |
| Compound | | RAGWE ED | VELVE TLEAF | S BAR LY LA | CORN FIELD | RICE, NATO | SOYBE AN HI | SUNFL R XXX | S WHE AT ER |
| 2-(4-Isopropyl-4- | | 9.0 | 9.0 | | | | | | |

TABLE IV-continued

| POST-EMERGENCE TESTS - RATES IN KG/HA | | | | | | | | |
|---|---|---|---|---|---|---|---|---|
| methyl-5-oxo-2- | 8.0 | 9.0 | | 9.0 | 9.0 | 9.0 | | |
| imidazolin-2-yl)- | 8.8 | 9.0 | 9.0 | 9.0 | 9.0 | 9.0 | 9.0 | 9.0 |
| nicotinic acid | 8.6 | 8.9 | 9.0 | 9.0 | 8.8 | 9.0 | 9.0 | 9.0 |
| | 8.6 | 8.9 | 9.0 | 9.0 | 8.8 | 9.0 | 9.0 | 9.0 |
| 2-(4-Isopropyl- | | 9.0 | | | | 0.5 | | |
| 4-methyl-5-oxo- | 9.0 | 9.0 | | 9.0 | 9.0 | 0.0 | 9.0 | 9.0 |
| 2-imidazolin-2- | 8.5 | 9.0 | | 9.0 | 9.0 | 0.1 | 9.0 | 9.0 |
| yl)-3-quinoline- | 8.8 | 8.6 | 9.0 | 9.0 | 8.7 | 3.0 | 9.0 | 8.9 |
| carboxylic acid | 8.0 | 8.3 | | | | 4.0 | | |
| | 8.4 | 7.7 | 9.0 | 9.0 | 8.3 | 2.7 | 9.0 | 8.8 |

EXAMPLE 9

Preemergence herbicidal evaluation of test compounds

The preemergence herbicidal activity of the compounds prepared by the process of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table V below. Where more than one test is involved for a given compound, the data are averaged.

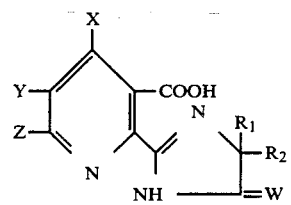

(IV)

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together along with the carbon to which they are attached, they may represent $C_3$–$C_6$ cycloalkyl optionally substituted with methyl, and when $R_1$ and $R_2$ are not the same, the optical isomers thereof; W is O or S; X is hydrogen, or $C_1$–$C_4$ alkyl, Y is hydrogen, halogen, $C_1$–$C_4$ alkyl, $C_1$–$C_4$ alkoxy, trifluoromethyl, trichloromethyl, difluoromethoxy, diloweralkylamino, $C_1$–$C_4$ alkylthio, nitro, phenyl or phenoxy optionally substituted with one $C_1$–$C_4$ alkyl, $C_1$–$C_4$ alkoxy or halogen; Z is hydrogen, $C_1$–$C_4$ alkyl, trifluoromethyl, trichloromethyl, phenyl or phenyl substituted with one $C_1$–$C_4$ alkyl,

TABLE V

| PRE-EMERGENCE TESTS - RATES IN KG/HA | | | | | | | | |
|---|---|---|---|---|---|---|---|---|
| Compound | RATE | BARNY ARDGR | GREEN FOX | P NUT SEDGE | WILD OATS | QUACK GRASS | FLD D IHOWO | MRNGL RY SP |
| 2-(4-Isopropyl-4- | 10.000 | 0.0 | 9.0 | 9.0 | 0.0 | | | 0.0 |
| methyl-5-oxo-2- | 2.000 | 9.0 | 9.0 | 9.0 | 9.0 | | | 0.0 |
| imidazolin-2-yl)- | 1.000 | 9.0 | 9.0 | 9.0 | 9.0 | 9.0 | 9.0 | 0.0 |
| nicotinic acid | .500 | 9.0 | 9.0 | 9.0 | 9.0 | 9.0 | 9.0 | 0.1 |
| | .250 | 9.0 | 9.0 | 9.0 | 9.0 | 9.0 | 9.0 | 8.8 |
| 2-(4-Isopropyl- | 8.000 | 9.0 | 9.0 | 9.0 | 9.0 | 9.0 | 9.0 | 0.0 |
| 4-methyl-5-oxo- | 4.000 | 9.0 | 9.0 | 9.0 | 9.0 | 9.0 | 9.0 | 9.0 |
| 2-imidazolin-2- | 1.000 | 9.0 | 9.0 | 9.0 | 9.0 | 9.0 | 9.0 | 9.0 |
| yl)-3-quinoline- | .500 | 0.0 | 9.0 | 9.0 | 0.9 | 9.0 | 9.0 | 0.6 |
| carboxylic acid | .250 | 0.3 | 0.8 | 9.0 | 0.6 | 9.0 | 9.0 | 0.0 |
| Compound | | RAGWE ED | VELVE TLEAF | S BAR LY LA | CORN FIELD | RICE, MATO | SOYBE AN HI | SUNFL R XXX | S WHE AT ER |
| 2-(4-Isopropyl-4- | | 0.0 | 0.0 | | | | 0.0 | | |
| methyl-5-oxo-2- | | 9.0 | 9.0 | | 9.0 | 9.0 | 0.0 | | |
| imidazolin-2-yl)- | | 9.0 | 9.0 | 9.0 | 9.0 | 9.0 | 0.5 | 9.0 | 9.0 |
| nicotinic acid | | 0.0 | 0.0 | 9.0 | 9.0 | 9.0 | 0.7 | 9.0 | 9.0 |
| | | 0.0 | 0.0 | 9.0 | 9.0 | 9.0 | 0.7 | 9.0 | 9.0 |
| 2-(4-Isopropyl- | | 9.0 | 0.0 | | | | | | |
| 4-methyl-5-oxo- | | 9.0 | 9.0 | | 9.0 | 9.0 | | 9.0 | 9.0 |
| 2-imidazolin-2- | | 9.0 | 8.8 | 9.0 | 9.0 | 9.0 | 6.5 | 9.0 | 9.0 |
| yl)-3-quinoline- | | 8.8 | 8.5 | 9.0 | 9.0 | 9.0 | 4.0 | 8.7 | 8.9 |
| carboxylic acid | | 7.9 | 7.9 | 9.0 | 8.8 | 9.0 | 3.6 | 0.6 | 0.6 |

What is claimed is:

1. In a process for the preparation of a 2-(4,4-disubstituted-5-oxo(or thiono)-2-imidazolin-2-yl)-nicotinic acid and 3-quinolinecarboxylic acids of the formula: $C_1$–$C_4$ alkoxy or halogen; and when taken together, Y and Z may form a ring in which YZ are represented by the structure: —$(CH_2)_n$—, where n is an integer from 3 to 5, provided that X is hydrogen; or YZ is

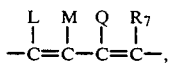

where L, M, Q and $R_7$ are each of hydrogen, halogen, $C_1$-$C_4$ haloalkyl, difluoromethoxy, diloweralkylamino, $C_1$-$C_4$ alkylthio, nitro, phenyl, phenoxy or mono-substituted phenyl or phenoxy where the substituent is $C_1$-$C_4$ alkoxy or halogen; with the proviso that only one of L, M, Q or $R_7$, may represent a substituent other than hydrogen, halogen, $C_1$-$C_4$ alkyl or $C_1$-$C_4$ alkoxy which comprises reacting a compound of the structure:

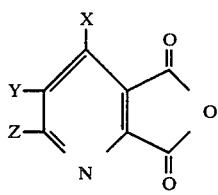

wherein X, Y and Z are as described above with a 1.0 to 1.5 equivalent, of a compound of the formula:

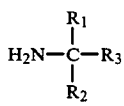

wherein $R_1$ and $R_2$ are as described above; $R_3$ is CN,

or

at a temperature between 5° and 45° C. under a blanket of nitrogen, to obtain 2-carbamoyl nicotinic and 3-quinolinecarboxylic acids of formula (I) having the structure;

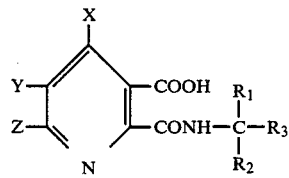

wherein X, Y, Z, $R_1$, $R_2$ and $R_3$ are as described above; treating the thus-formed reaction product with 2 to 10 moles of aqueous or aqueous $C_1$-$C_4$ alcoholic sodium or potassium hydroxide; and when $R_3$ is CN, 2 to 5 moles of 30 to 90% aqueous hydrogen peroxide per mole of formula (I) compound, at a temperature of 25° to 110° C., acidifying the thus-formed reaction mixture to a pH between 1.5 and 4 with hydrochloric acid or sulfuric acid, and isolating the product by filtration or extraction of the acidified reaction mixture with an organic solvent and separating the solvent from the formula (IV) product, the improvement comprising carrying out the reaction for preparing the formula (I) product in the presence of a minimum of 4 molar equivalents of pyridine, 4-picoline, 2-picoline, 3-picoline, mixed picolines, quinoline, or a lutidine, either alone or in the presence of a hydrocarbon co-solvent.

2. In a method for the preparation of substituted and unsubstituted 2-carbamoyl nicotinic and 3-quinolinecarboxylic acids of formula (I):

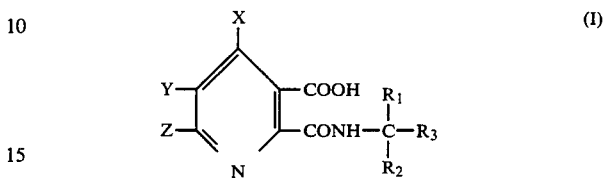

wherein $R_1$ is $C_1$-$C_4$ alkyl; $R_2$ is $C_1$-$C_4$ alkyl or $C_3$-$C_6$ cycloalkyl; and when $R_1$ and $R_2$ are taken together along with the carbon to which they are attached, they may represent $C_3$-$C_6$ cycloalkyl optionally substituted with methyl, and when $R_1$ and $R_2$ are not the same, the optical isomers thereof; $R_3$ is CN or

W is O or S; X is hydrogen, or $C_1$-$C_4$ alkyl, Y is hydrogen, halogen, $C_1$-$C_4$ alkyl, $C_1$-$C_4$ alkoxy, trifluoromethyl, trichloromethyl, difluoromethoxy, diloweralkylamino, $C_1$-$C_4$ alkylthio, phenyl or phenoxy or phenyl or phenoxy substituted with one $C_1$-$C_4$ alkyl, $C_1$-$C_4$ alkoxy or halogen; Z represents hydrogen, $C_1$-$C_4$ alkyl, trifluoromethyl, trichloromethyl, phenyl or phenyl substituted with one $C_1$-$C_4$ alkyl, $C_1$-$C_4$ alkoxy or halogen; and when taken together, Y and Z may form a ring in which YZ are represented by the structure: $-(CH_2)_n-$, where n is an integer of 3 to 5, provided that X is hydrogen; or YZ is

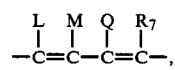

where L, M, Q and $R_7$ are each of hydrogen, halogen, $C_1$-$C_4$ alkyl, $C_1$-$C_4$ alkoxy, $C_1$-$C_4$ haloalkyl, difluoromethoxy, diloweralkylamino, $C_1$-$C_4$ alkylthio, nitro, phenyl, phenoxy or mono-substituted phenyl or phenoxy where the substituent is one $C_1$-$C_4$ alkyl, $C_1$-$C_4$ alkoxy or halogen; with the proviso that only one of L, M, Q or $R_7$, may represent a substituent other than hydrogen, halogen, $C_1$-$C_4$ alkyl or $C_1$-$C_4$ alkoxy which comprises reacting an anhydride of formula (II)

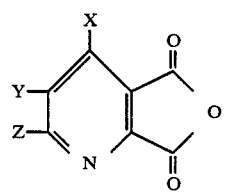

wherein X, Y and Z are as described above with from 1.0 to 1.5 molar equivalents of an aminonitrile, aminocarboxamide, or aminothiocarboxamide of formula III:

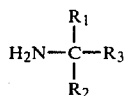

wherein $R_1$, $R_2$ and $R_3$ are as described above at from 5° to 45° C., the improvement comprising carrying out the reaction in a solvent system containing a minimum of 4 molar equivalents of pyridine, 4-picoline, 2-picoline, 3-picoline, mixed picolines, quinoline, or a lutidine, used either as the reaction solvent or as a co-solvent, with other organic solvents, for several hours.

3. A method according to claim 2, wherein the reaction solvent is 6 to 10 molar equivalents of pyridine, 4-picoline, 2-picoline, mixed picolines or quinoline.

4. A method according to claim 2, wherein the reaction solvent is a mixture of toluene containing 6 to 10 molar equivalents of pyridine, 4-picoline, 2-picoline, mixed picolines or quinoline.

5. A method according to claim 2, wherein the reaction is conducted in a temperature range of 5° to 30° C.

6. A method according to claim 5, for the preparation of 2-[(1-carbamoyl-1-2-dimethylpropyl)-carbamoyl]-nicotinic acid.

7. A method according to claim 5, for the preparation of 2-[(1-carbamoyl-1,2-dimethylpropyl)-carbamoyl]3-quinolinecarboxylic acid.

8. A method according to claim 5, for the preparation of 2-[(1-cyano-1,2-dimethylpropyl)carbamoyl]-nicotinic acid.

9. A method according to claim 5, for the preparation of 2-[(1-cyano-1,2-dimethylpropyl)carbamoyl]3-quinolinecarboxylic acid.

* * * * *